United States Patent [19]

Lauterbach et al.

[11] Patent Number: 5,132,471
[45] Date of Patent: Jul. 21, 1992

[54] PURIFICATION OF α-BISABOLOL

[75] Inventors: Gerald Lauterbach, Bensheim; Otto Hertel; Klaus Euler, both of Ludwigshafen, all of Fed. Rep. of Germany

[73] Assignee: BASF Aktiengesellschaft, Ludwigshafen, Fed. Rep. of Germany

[21] Appl. No.: 690,617

[22] Filed: Apr. 24, 1991

[30] Foreign Application Priority Data

Apr. 24, 1990 [DE] Fed. Rep. of Germany ....... 4012945

[51] Int. Cl.⁵ ...................... C07C 35/18; C07C 33/14
[52] U.S. Cl. .................................. 568/826; 568/825; 568/827; 568/828
[58] Field of Search ............... 568/827, 826, 822, 823, 568/825, 826

[56] References Cited

U.S. PATENT DOCUMENTS 3,932,533  1/1976  Isaac ..................... 568/827

FOREIGN PATENT DOCUMENTS 0247495  10/1989  Japan ..................... 568/826

Primary Examiner—Werren B. Lone
Attorney, Agent, or Firm—Oblon, Spivak, McClelland, Maier & Neustadt

[57] ABSTRACT

α-Bisabolol is purified by distilling a plant extract containing α-bisabolol under reduced pressure and drawing off the purified α-bisabolol in the lower half of a distillation column as side product, and feeding in the extract above the side outlet.

4 Claims, No Drawings

PURIFICATION OF α-BISABOLOL

The present invention relates to a novel process for purifying α-bisabolol by distillation of a plant extract containing α-bisabolol under reduced pressure.

α-Bisabolol is a sesquiterpene alcohol of the following formula

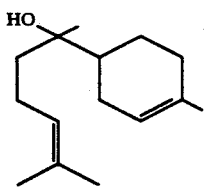

which occurs in four stereoisomeric forms.

DE-A 2 317 583 and EP-A 253 922 disclose processes for obtaining and purifying α-bisabolol from plant extracts, in which the extracts are prepurified by washing with alkaline solutions and treatment with active carbon or by filtration through an ion exchange resin and subsequently subjected to a distillation. Both publications point out that α-bisabolol cannot be purified by distillation alone.

It is an object of the present invention, since these processes are very industrially elaborate, to provide a more straightforward and economic process for purifying α-bisabolol.

We have found that this object is achieved by a process in which a plant extract containing α-bisabolol is distilled under reduced pressure, wherein the purified α-bisabolol is taken off as side product in the lower half of a distillation column, and the extract is fed in above the side outlet.

The extracts containing α-bisabolol can be isolated by conventional methods from various plants such as Matricaria chamomilla (M.A. Schwartz, G.C. Swanson; J. Org. Chem. 44 (1979) 953) and, preferably, from Vanillosmopsis erythropappa (B.R. Gottlieb, M.T. Magalhaes; Perf. Essent. Oil. Rec. (1958) 711). The extract isolated from Vanillosmopsis erythropappa is called candeia oil.

As a rule, the crude extracts contain from 70 to to 90% by weight of α-bisabolol. The other constituents are substances with an unpleasant odor and unacceptable color such as isovaleric acid, bisabolene and eremanthine.

The distillation columns suitable for the novel process usually have from 6 to 50, in particular 10 to 30, theoretical plates. The design of the column is unimportant, ie. bubble plate, sieve plate, valve plate and grid plate columns or, preferably, packed columns can be used.

In the case of packed columns, all conventional packings can be employed such as Raschig rings, Pall rings or metal packings.

The crude extract is preferably fed into the column in the region of two thirds of its height. The place where the α-bisabolol is removed is in the region of the first third of the height of the column and is not less than 2 theoretical plates below the place where the crude extract is fed in. Normally the inlet and side outlet are arranged so that in each case from 2 to 20 theoretical plates are located between them and between the column bottom and the side outlet.

The reflux ratio is suited to the required product quality by selecting it as a rule in the range from 2:1 to 20:1, preferably in the range from 3:1 to 12:1.

The extracts are fractionated in particular in the pressure range from 0.01 to 50 mbar, preferably 0.05 to 5 mbar, corresponding to a temperature in the range from 110° to 200° C.

The overhead product comprises about 5 to 25% by volume of the extract which is fed in, and usually contains all the malodorous subsidiary components.

The column bottom can be heated by conventional industrial means, for example a thin-film evaporator.

The α-bisabolol purified in this way can be employed without further treatment as a fixative for scents or in cosmetics.

The novel process can be used to purify all the stereoisomers of α-bisabolol, isolated or as mixtures.

The process is straightforward to implement and not environmentally deleterious and provides the required product in high yields.

EXAMPLE 8 kg of candeia oil which contained 80% by weight of (−)-α-bisabolol were fed each hour into a column with a height of 1.70 m and a diameter of 0.15 m and with 18 theoretical plates, which was packed with a metal packing (CY supplied by Sulzer AG), the pressure at the head being 0.3 to 0.5 mbar, at the level of the 12th plate (counted from the bottom) and at 128° to 132° C.

The column was heated using a heat-transfer oil. In addition, the bottom phase was heated with a thin-film evaporator.

At a reflux ratio of 6:1, the overhead product (85° C.) was 1.5 kg of distillate, the bottom product (240° C.) weighed 0.5 kg, and 6 kg of (−)-α-bisabolol vapor were obtained at the level of the 6th plate and at 130 to 138° C., per hour.

The distillation yield of (−)-α-bisabolol was thus 94% based on its content in the candeia oil employed.

The (−)-α-bisabolol obtained in this way had a purity of 97% and could be used in this form directly for manufacturing cosmetics.

We claim:

1. A process for purifying α-bisabolol from a crude plant extract containing α-bisabolol, comprising distilling said crude plant extract containing α-bisabolol under reduced pressure in a distillation column having an inlet and a side outlet located in the lower half of the distillation column, said inlet being located above said side outlet, feeding said plant extract containing α-bisabolol into said inlet and recovering purified α-bisabilol from said side outlet.

2. A process for purifying α-bisabolol as claimed in claim 1, wherein the inlet is located in the region of two third of the height of the distillation column and the side outlet is located in the region of the first third of the height of the distillation column and not less than two theoretical plates below the location of the inlet.

3. A process for purifying α-bisabolol as claimed in claim 1, wherein in each case from 2 to 20 theoretical plates are located in said distillation column between the inlet and side outlet and between the bottom of the distillation column and the side outlet.

4. A process for purifying α-bisabolol as claimed in claim 1, wherein the pressure in the distillation column is in the range form 0.01 to 50 mbar corresponding to a temperature in the range from 110° to 200° C.

* * * * *